United States Patent
Cen et al.

(10) Patent No.: US 7,846,105 B2
(45) Date of Patent: *Dec. 7, 2010

(54) NON-INVASIVE BLOOD PRESSURE MEASUREMENT SAFETY PROTECTION METHOD AND APPARATUS

(75) Inventors: Jian Cen, Shenzhen (CN); Xiaoyu Wu, Shenzhen (CN); He Bo, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 12/507,632

(22) Filed: Jul. 22, 2009

(65) Prior Publication Data

US 2009/0287098 A1   Nov. 19, 2009

Related U.S. Application Data

(63) Continuation of application No. 11/607,403, filed on Nov. 30, 2006, now Pat. No. 7,594,892.

(30) Foreign Application Priority Data

Jul. 11, 2006   (CN) .................. 2006 1 0061664

(51) Int. Cl.
*A61B 5/00*   (2006.01)
(52) U.S. Cl. .................. 600/490; 600/494; 600/496
(58) Field of Classification Search .................. None
See application file for complete search history.

(56) References Cited

U.S. PATENT DOCUMENTS

| | | | |
|---|---|---|---|
| 4,747,412 A | 5/1988 | Yamaguchi | |
| 4,796,184 A | 1/1989 | Bahr et al. | |
| 4,953,557 A | 9/1990 | Frankenreiter et al. | |
| 5,240,008 A | 8/1993 | Newell | |
| 5,241,964 A | 9/1993 | McQuilkin | |
| 7,594,892 B2 * | 9/2009 | Cen et al. | 600/490 |
| 2007/0142731 A1 | 6/2007 | Ye et al. | |

FOREIGN PATENT DOCUMENTS

| | | |
|---|---|---|
| CN | 2688226 Y | 3/2005 |
| CN | 1608583 A | 4/2005 |
| CN | 2707188 Y | 7/2005 |
| CN | 1761426 A | 4/2006 |
| CN | 1778269 | 5/2006 |
| CN | 1513417 A1 | 7/2007 |

* cited by examiner

*Primary Examiner*—Robert L Nasser
(74) *Attorney, Agent, or Firm*—Kory D. Christensen; Stoel Rives LLP

(57) ABSTRACT

The present invention discloses a non-invasive blood pressure measurement apparatus and a safety protection method. In addition to a main pressure measurement circuit and a main microprocessor circuit, the measurement apparatus also includes an independently disposed assist pressure measurement circuit and an independently disposed assist microprocessor circuit. In normal measurement, the assist microprocessor circuit periodically samples a cuff pressure via the assist pressure measurement circuit, and compares the measured cuff pressure with a specified overpressure protection value, and if the cuff pressure exceeds the specified overpressure protection value, the assist microprocessor circuit outputs a control signal to open a deflation valve until the pressure falls to below the safety pressure. Compared with the prior art, the method for overpressure protection of the present invention is more direct and has higher accuracy of decision, leading to higher reliability of the overpressure protection and higher safety of the measurement apparatus.

14 Claims, 3 Drawing Sheets

NON-INVASIVE BLOOD PRESSURE MEASUREMENT SAFETY PROTECTION METHOD AND APPARATUS

This application is a continuation of U.S. application Ser. No. 11/607,403, filed Nov. 30, 2006, now U.S. Pat. No. 7,594,892.

TECHNICAL FIELD

The present invention relates to a medical device and particularly to a non-invasive blood pressure measurement apparatus and safety protection method implemented by the non-invasive blood pressure measurement apparatus.

BACKGROUND ART

The non-invasive blood pressure measurement function is one of the most basic monitor parameters of the monitors, and a key parameter reflecting the performance characteristic of the monitors. The measurement methods currently utilized in most of the monitors are based on oscillation method. Those methods are popularly applied in clinic because they are convenient in practice with impersonal measurement results and good repeatability.

The oscillation method is a method of inflating the cuff wound around an arm by an air pump so as to interrupt the propagation of pulses in blood vessels, then, deflating the cuff step by step in linear mode (3-5 mmHg/s) or in step mode (6-15 mmHg/step), and converting a pulse signal and a pressure signal, which are transferred to air path via the cuff, into digital signals by the aid of a bridge pressure sensor connected to the air path and corresponding amplifying circuit, filter circuit, A-D converter (analog-to-digital converter), microprocessor control and the like; further, performing proper data process for signals of the pulse wave and the cuff pressure to achieve a series of pulse waves containing a transforming tendency of the pulse waves and a corresponding cuff pressure; and then, using the cuff pressure at the highest pulse as an average pressure of a testee, and calculating the desired results such as a systolic pressure, a diastolic pressure and an average pressure by utilizing some empirical proportional coefficient algorithm.

Because the non-invasive blood pressure measurement method is an indirect measurement method, which requires applying pressure to an upper arm via a cuff for interrupting the propagation of pulses in the blood vessels during measurement process, if the cuff pressure and the measurement time are not properly controlled, the human body might be hurt. For this reason, some detailed international standards have been set for the designing and evaluating of the safety and effectiveness of the blood pressure measurement functions, such as ANSI/AAMI SP10:2002 and IEC 60601-2-30:1999(E) standards. The two standards particularly put forward the requirements for safety as follows:

(1) The maximum cuff pressure obtainable in NORMAL USE shall not exceed 300 mmHg for EQUIPMENT specified for adult PATIENTS ("Adult") and 150 mmHg for EQUIPMENT specified for use on infant PATIENTS ("Infant").

(2) In any SINGLE FAULT CONDITION, means shall be provided, functioning independently of the normal pressure control system, which a) shall prevent the pressure in the cuff from exceeding the maximum NORMAL USE values specified in (1) by more than +10%, and b) shall activate if the pressure in the cuff exceeds the maximum NORMAL USE values specified in (1) for 15 s.

When being activated, this means shall deflate the cuff to 15 mmHg for adults or 5 mmHg for neonates within 30 s.

SINGLE FAULT CONDITION means any one of the following conditions: a) results in a failure of the normal pressure regulating means, or, b) prevents deflation of the cuff within the specified period, or, c) results in a failure of the normal cuff pressurization timing.

(3) In any mode of operation, including any SINGLE FAULT CONDITION described above, the cuff shall not be inflated above 15 mmHg for more than 180 s for EQUIPMENT specified for use on adult PATIENTS, and shall not be inflated above 5 mmHg for more than 90 s for EQUIPMENT specified for use on infant PATIENTS.

(4) In LONG TERM AUTOMATIC MODE, cuff pressure shall be released for at least 30 s after each period of cuff pressure above 15 mmHg for EQUIPMENT specified for use on adult PATIENTS, or 5 mmHg for EQUIPMENT specified for use on infant PATIENTS, except when the total duration of the alternating inflation/deflation periods does not exceed the maximum inflation time specified in (3). After this the cuff pressure shall be released to below the pressure stated for at least 30 s.

(5) In LONG TERM AUTOMATIC MODE, means shall be provided in any SINGLE FAULT CONDITION as described in (2), functioning independently of the normal timing control system, which, if the deflated period is less than 30 s, will release cuff pressure to below 15 mmHg for EQUIPMENT specified for use on adult PATIENTS, or below 5 mmHg for EQUIPMENT specified for use on infant PATIENTS.

The current safety protection method implemented by the non-invasive blood pressure measurement circuit, such as a Chinese application No. CN03139708.5 entitled "An Electric Non-Invasive Blood Pressure Measurement Apparatus (☐☐☐☐☐☐☐☐☐)," detects the cuff pressure with an additional pressure sensor, and achieves the overpressure protection under SINGLE FAULT CONDITION by controlling a fast deflation valve with use of a simple comparator. In this method, the "adult" mode and the "infant" mode are distinguished by two comparative levels. Since the calibration of these comparative levels is performed by a potentiometer, which has to be disassembled for calibration, leading to inconvenience. In addition, the overpressure protection point may drift following the voltage of power supply and the drift voltage of the sensor, so the timing function can not be realized independently.

In a Chinese application No. CN200410051173.2 entitled "A Improved Electric Blood Pressure Measurement Method And Apparatus (☐☐☐☐☐☐☐☐☐☐☐☐)", a microprocessor is added to realize independent timing. However, the overpressure protection of the apparatus is still based on controlling deflation of the valve with use of a comparator, and the added microprocessor is used only as an independent timer, and can not estimate the internal pressure of the cuff. Although the apparatus can realize simple function of overpressure protection, it cannot estimate threshold value under SINGLE FAULT CONDITION such as 15 mmHg or 5 mmHg for measuring channel fault. In this application, the pressure measurement circuit for overpressure protection has no calibration function, and the drift caused by its sensor and power supply will lead to drift of the overpressure protection point, so larger error may be obtained.

DISCLOSURE OF THE INVENTION

The present invention has been made to overcome such disadvantageous as described above and provides a safety protection method and an apparatus implanting it with higher safety, active safety protection, and completely satisfy the related international standards for the non-invasive blood pressure measurement.

A non-invasive blood pressure measurement apparatus comprises a cuff, a main measurement circuit, and a safety protection circuit; wherein said main measurement circuit comprises a main pressure measurement circuit for collecting a cuff pressure signal of said cuff; a main microprocessor circuit, for receiving said cuff pressure signal from said main pressure measurement circuit and calculating the value of said cuff pressure; an air pump; an air pump control circuit, for receiving a control signal from said main pressure measurement circuit and controlling open/close of said air pump; a deflation valve; a deflation valve control circuit, for receiving a control signal from said main pressure measurement circuit and controlling open/close of said deflation valve; said safety protection circuit comprises an assist pressure measurement circuit, for collecting a cuff pressure signal of said cuff in real-time; and an assist microprocessor circuit, for outputting a control signal to said deflation valve control circuit depending on the cuff pressure signal received from said assist pressure measurement circuit, and controlling open/close of said deflation valve via said deflation valve control circuit.

The present invention in another aspect provides a safety protection method implemented by a non-invasive blood pressure measurement apparatus, comprising: for normal measurement process in which said main pressure measurement circuit collects a cuff pressure signal of a cuff and inputs it to said main microprocessor circuit and then said main microprocessor circuit calculates said cuff pressure, said assist pressure measurement circuit samples a cuff pressure signal then said assist microprocessor circuit outputs a control signal to a deflation valve control circuit depending on the cuff pressure signal received from said assist pressure measurement circuit, and controls open/close of said deflation valve via said deflation valve control circuit.

The following beneficial effects are achieved by applying the solutions mentioned above:

The additional assist microprocessor circuit independently analyzes and decides the sampled cuff pressure signal, therefore the method for performing overpressure protection, compared with the prior art, is more direct, and has higher accuracy of decision, leading to higher reliability of the overpressure protection and higher safety of the measurement apparatus. Meanwhile, the present assist microprocessor circuit combines timing protection with pressure measurement, and it is completely independent from the main microprocessor circuit, so it can perform the decision of the pressure point, as well as decide a plurality of threshold points, and automatically eliminate null drift, so its accuracy is high. Furthermore, the assist microprocessor circuit of the invention can eliminate impact to the precision of pressure sampling arisen from voltage fluctuation of the power supply by monitoring the voltage of power supply in real-time.

In the present invention, setting an overpressure protection voltage only relates to software process and the information about the overpressure protection voltage is stored in a Flash or EEPROM. Compared with the design of the prior art, the apparatus of the invention does not need to be disassembled at time of overpressure protection calibration, and is more flexible and more reliable.

In the present invention, setting a measurement mode such as "Adult" and "Infant" mode can be performed independently with the assist microprocessor circuit through keys, or through a command acquired from an upper computer, thus completely independent from the main microprocessor circuit, avoiding the risk of error in timing and overpressure protection point of the main microprocessor which are caused by the operation that the infant mode is wrongly set as the adult mode. When the program of the main microprocessor is dead, running out of control, and the main microprocessor circuit cannot work normally, the assist microprocessor circuit forcibly reset the main microprocessor circuit and open the deflation valve for ensuring safe.

The additionally provided functions of monitoring the cuff pressure and the operating state of the air pump, air deflating for safety protection, and the independent timing in combination with measurement of the cuff pressure, have realized all the safety protection functions required by related standards (ANSI/AAMI SP10:2002 and IEC 60601-2-30:1999 (E) standards) at module level.

The apparatus of the invention is highly integrated, and suitable for small and portable equipments.

BEST MODES FOR CARRYING OUT THE INVENTION

Figure 1:
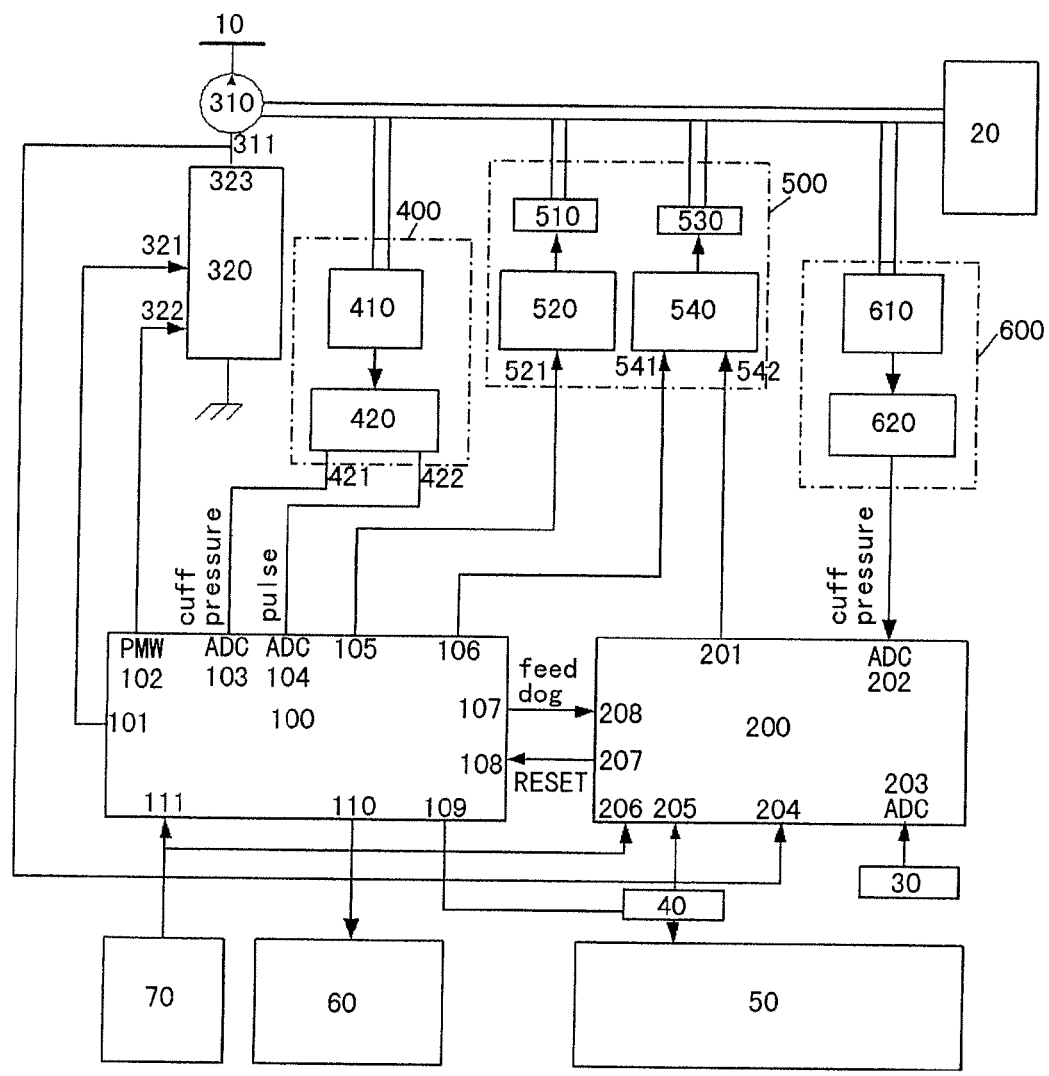
FIG. 1 is a block diagram showing the system of a preferred embodiment of the non-invasive blood pressure measurement apparatus of the present invention.

Hereinafter the present invention in embodiment will be described in more detail with reference to the drawing.

With reference to FIG. 1, a non-invasive blood pressure measurement apparatus comprises a main microprocessor circuit 100, an assist microprocessor circuit 200, an air pump 310 and an air pump control circuit 320, a main pressure measurement circuit 400, an assist pressure measurement circuit 600, an deflation valve and an deflation valve control circuit 500, a display module 60, a communication interface module 40, and a key module 70. Wherein, the main microprocessor circuit 100 performs the whole process of the non-invasive blood pressure measurement and control, and finally outputs a non-invasive blood pressure measurement value. The assist microprocessor circuit 200 performs the functions of monitoring a cuff pressure and an operating state of the air pump 310, and deflation for safety protection. The deflation valve and the deflation valve control circuit 500 comprises a slow deflation valve 510 and a slow deflation valve control circuit 520, as well as a fast deflation valve 530 and a fast deflation valve control circuit 540. The main pressure measurement circuit 400 comprises a main pressure sensor 410, and a main amplifying circuit 420. The assist pressure measurement circuit 600 comprises an assist pressure sensor 610, and an assist amplifying circuit 620.

The main microprocessor circuit 100 comprises a microprocessor, an A-D converter, a memory, and the like, generates air pump control signal and deflation valve control signal for controlling the whole measurement process and performs the sampling of the cuff pressure signal and the pulse wave signal via the A-D converter. Based on the above sampling results, the main microprocessor can achieve results such as a systolic pressure, a diastolic pressure, an average pressure and a pulse rate by utilizing a certain algorithm.

The main microprocessor circuit 100 has an air pump control port 101 and an PWM 102 connected to the ports 321 and 322 of the air pump control circuit 320 respectively; ADC 103 and 104 connected to the ports 421 and 422 of the main amplifying circuit 420; a slow deflation control port 105 connected to the slow deflation valve control circuit 520; a fast deflation control port 106 connected to the input port 541 of the fast deflation valve control circuit 540; a feed-dog signal output port 107 connected to the signal input port 208 of the assist microprocessor circuit 200; a RESET signal input port 108 connected to the signal output port 207 of the assist microprocessor circuit 200; and ports 109, 110 and 111 connected to the communication interface module 40, the display module 60, and the key module 70 respectively.

The assist microprocessor circuit 200 comprises a microprocessor, an A-D converter, and a Flash or EEPROM memory. Because this part of the circuit is a redundant design for safety protection, its sampling result will not be used for the measurement of blood pressure value, thus the performance of the microprocessor and the resolution of the A-D converter doesn't necessarily to be high. Even an 8-bit Single Chip Micyoco, an 8-bit or 10-bit A-D converter may be adoptable. This part of the circuit is used for carrying out a separate detection of the cuff pressure, wherein the memory is used to store a calibrated value of the overpressure protection pressure. The main microprocessor circuit and the assist microprocessor circuit may utilize a Single Chip Micyoco integrated with an A-D converter and a flash memory, such as MSP430 from TI and LPC2131 from PHLIPS; they can also be implemented in the form of an externally connected EEPROM, such as 25AA640 from Microchip.

The assist microprocessor circuit 200 has a fast deflation control port 201 connected to the input port 542 of the fast deflation valve control circuit 540; ADC port 202 connected to the assist pressure measurement circuit 600, for receiving a cuff pressure signal sampled by the assist pressure measurement circuit 600; ADC port 203 connected to the power supply 30, for sampling a voltage signal from the power supply 30; air pump state monitoring port 204 connected to air pump control signal input port 323 of the air pump control circuit 320; ports 205 and 206 connected to the communication interface module 40 and the key module 70 respectively; control signal output port 207 connected to the RESET signal input port 108 of the main microprocessor circuit 100; signal input port 208 connected to the feed-dog signal output port 107 of the main microprocessor circuit 100.

Figure 2:
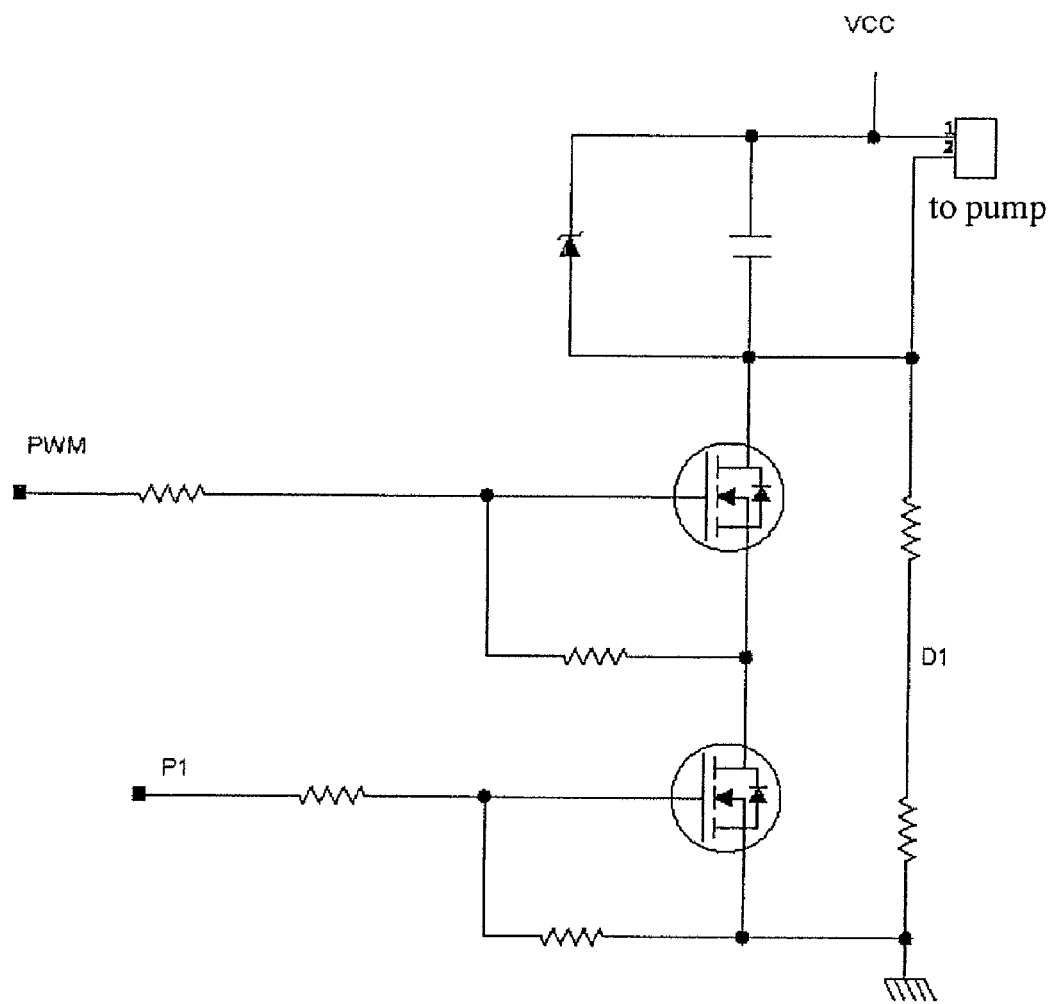
FIG. 2 shows a control and monitor circuit for the air pump of the non-invasive blood pressure measurement apparatus of the present invention.

The air pump 310 and the air pump control circuit 320 are shown in FIG. 2. As shown, the air pump 310 is connected to the power supply at one end, and connected to ground at the other end via two MOS transistors. The PWM and P1 are respectively PWM signal and air pump control signal of the main microprocessor circuit 100. When both of the signals are at high level, the two MOS transistors are turned on, and the air pump will inflate air. So, only when the main microprocessor air pump control signal P1 and the PWM control signal simultaneously act, does the enabling turning-on of the air pump be valid, thus to avoid the case that the air pump control circuit 320 cannot stop the inflation of the air pump under the SINGLE FAULT CONDITION. When the air pump is operating, the level of the air pump control port is pulled down, and this signal will be sent to the assist microprocessor circuit 200 for sampling via the node D1 with voltage divided by resistors. If a low level is sampled, the assist microprocessor circuit 200 may decide that the air pump 310 is in operating state. In this way, the assist microprocessor circuit 200 can obtain the operating state of the air pump in real-time. If the air pump 310 keeps operating when the system is not in measurement state, the assist microprocessor circuit 200 outputs RESET signal to reset the main microprocessor circuit 100, and after being reset, the main microprocessor circuit 100 opens the fast deflation valve and closes the air pump, waiting for the next measurement.

The main pressure measurement circuit 400 comprises a main pressure sensor 410 and a main amplifying circuit 420 for performing measurement of the cuff pressure and the pulse wave and finally sending the measured results to the A-D converter of the main microprocessor circuit 100 for analog-to-digital conversion.

The deflation valve and the deflation valve control circuit 500 comprises a slow deflation valve 510 and a slow deflation valve control circuit 520, as well as a fast deflation valve 530 and a fast deflation valve control circuit 540. The slow deflation valve control circuit 520 controls open/close of the slow deflation valve 510 and carries out deflating air in linear mode or in step mode during the measurement process. The control signal for the slow deflation valve 510 is provided only by the main microprocessor circuit 100. In the case that the cuff pressure exceeds the safety pressure, the fast deflation valve control circuit 540 controls the fast deflation valve 530 to open, enabling the cuff pressure to be quickly released to below the safety pressure. Wherein, the fast deflation valve 530 is a normally open valve and the main microprocessor circuit 100 and the assist microprocessor circuit 200 are provided with a fast deflation valve control port 106 and 201 respectively for opening the fast deflation valve 530 independently. And, the close of the fast deflation valve 530 needs the main microprocessor circuit and the assist microprocessor circuit outputting close signal simultaneously. In normal measurement, the fast deflation valve 530 should be closed.

The assist pressure measurement circuit 600 comprises an assist pressure sensor 610 and an assist amplifying circuit 620. This circuit is not required for detecting pulse wave, so it has a relatively simple structure that needs only one stage amplifying circuit. Meanwhile, this circuit is designed only for safety control, so it may choose a sensor with lower performance than that of the main measurement circuit.

The key module 70 may be used as an input means by which the corresponding commands are input when the measurement is started/paused, or by which the measurement mode, such as "Adult" or "Infant" mode, is input into the assist microprocessor circuit.

The display module 60 is used to display measurement results such as the cuff pressure, as well as alarm information, etc. The apparatus, equipped with the display module 60, can form an independent portable blood pressure measurement apparatus powered by batteries. Also, the apparatus can be used as a parameter module for medical equipment such as a monitor.

The communication interface 40 is such an interface by which the apparatus communicates with an upper computer when the apparatus is used in an equipment (for example, a monitor) as a parameter module, or such an interface by which the apparatus communicates with an upper computer equipment such as a PC computer when the apparatus functions as a portable blood pressure measurement apparatus, for setting the overpressure point and uploading the trend data, etc. This interface may be a RS232 serial interface, a USB interface or a blue-tooth interface, and the like.

The main measurement circuit monitors the cuff pressure and measurement time according to the safety requirement of the above standard, and in case that overpressure, overtime, etc. occurs, the main measurement circuit stops measurement, and opens the deflation valve and closes the air pump. The safety protection circuit constructed by the assist microprocessor circuit provides safety protection function under SINGLE FAULT CONDITION caused by the main measurement circuit.

Figure 3:
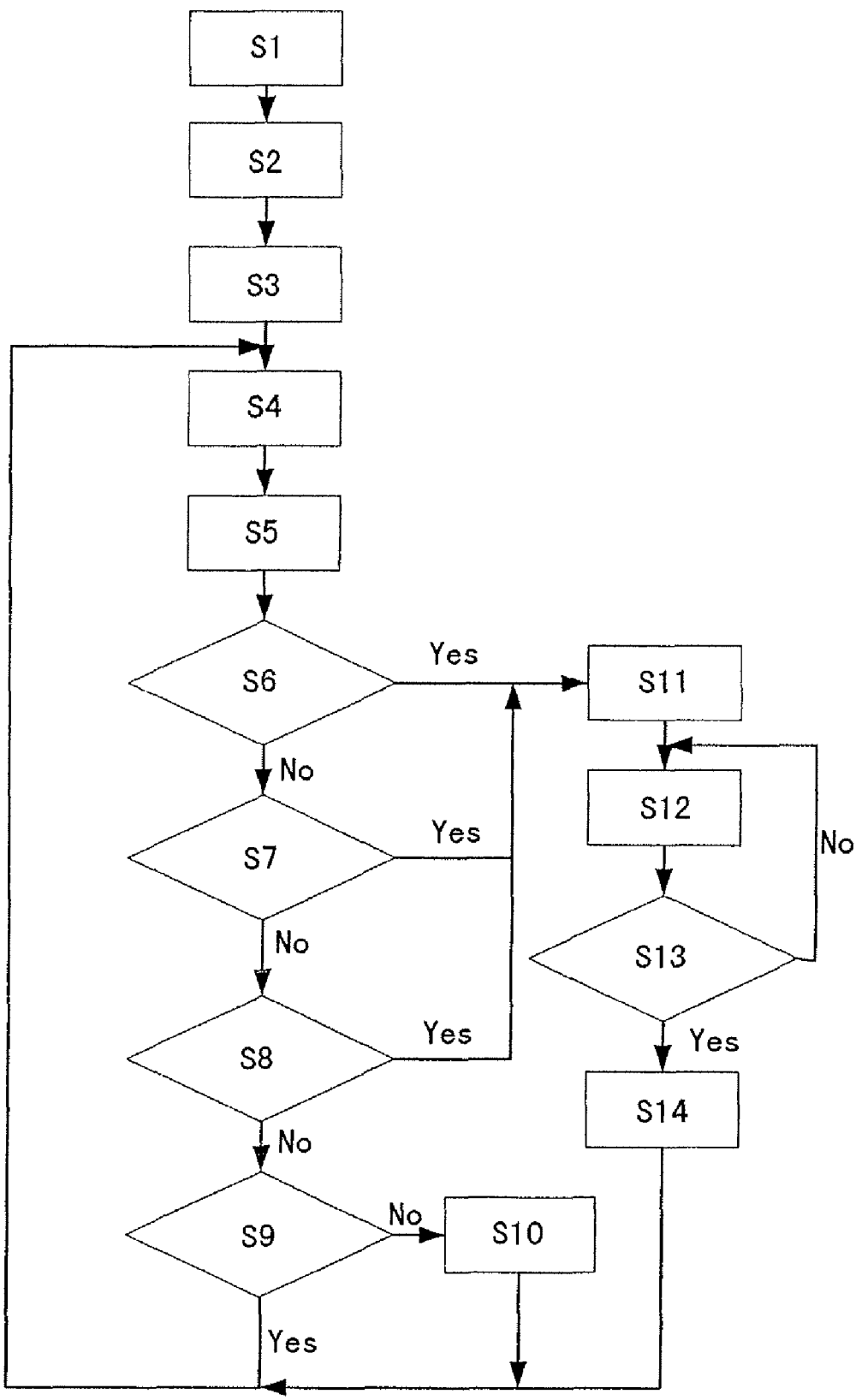
FIG. 3 is a flowchart illustrating a preferred embodiment of the safety protection method of the non-invasive blood pressure measurement apparatus of the present invention.

The specific flow for the safety protection of the safety protection circuit is shown in FIG. 3, wherein the control flow of the main microprocessor circuit 100 is substantially same as the control flow of the non-invasive blood pressure measurement of the prior art. The assist microprocessor circuit 200 of the safety protection circuit can realize the following functions:

Set of Overpressure Protection Point:

Because of drift and discreteness of the sensors and detection circuits, the overpressure protection point of the non-invasive blood pressure measurement apparatus should be set before first use. Firstly, the assist microprocessor circuit 200 should be internally provided or externally combined with a nonvolatile memory, such as a Flash, an EEPROM, and the like. Secondly, when being set, the cuff pressure is set as the pressure of the overpressure protection point for different patient modes: 320 mmHg for "Adult" mode, and 160 mmHg for "Infant" mode (for meeting the requirement of the standards: not exceeding the maximum NORMAL USE values specified in (1) by more than +10%); and then, the assist microprocessor circuit 200 is informed to write the sampled values into the nonvolatile memory; and the setting commands can be input by keys, or be sent by the upper computer via a communication interface 40 connected to the upper computer 50. Afterward, the sampled values stored in the nonvolatile memory will be used as standard for the latter overpressure protection.

Overpressure Protection:

At time of setting the overpressure protection point, the calibration will be performed at two pressure points of 320 mmHg and 160 mmHg. Linear coefficients of the sensor can be achieved by use of the linear property of the pressure sensor; and furthermore, the monitoring to the minimum safe air pressure value (15 mmHg for "Adult", 5 mmHg for "Infant") can be achieved by the assist microprocessor circuit 200.

The safe protect method of the present invention will be described in more detail referring to FIG. 3.

Firstly, every time the apparatus is powered up, the assist microprocessor circuit 200 will open the fast deflation valve 510 (S1), so that the cuff communicate with the atmospheric, and the atmospheric pressure at that time is measured for eliminating the null drift of the circuit (S2). And then, the assist microprocessor circuit 200 outputs a signal for closing the fast deflation valve 530 (S3). In normal measurement, the assist microprocessor circuit 200 will periodically sample the cuff pressure (for example, once a second) (S4), and corrects the measurement result, that is, calculates the real-time pressure value based on the linear property of the assist microprocessor circuit 200 (S5). Then, the assist microprocessor circuit 200 compares the corrected real-time pressure value with a predetermined overpressure protection value (320 mmHg for "Adult", 160 mmHg for "Infant") (S6). If the predetermined value is exceeded, the assist microprocessor circuit 200 will determine an overpressure condition and open the fast deflation valve until the pressure is released to below the safety pressure (15 mmHg for "Adult", 5 mmHg for "Infant") (S11). If the assist microprocessor circuit 200 cannot lower the cuff pressure to below the safety pressure within 30 seconds, it may reset the main microprocessor circuit 100 (S11).

It is easy to control the precision of sampling by use of the A-D converter, and it is easy to meet the precision of 10☐ overpressure protection required by the standards by combining with monitoring the power supply and eliminating the fluctuation effects of the power supply.

Control of Measurement Time:

Every time the apparatus is powered up, the assist microprocessor circuit 200 will open the fast deflation valve 530, and sample the cuff pressure when the pressures inside and outside the cuff are same, so as to eliminate null drifts of the sensor and the detection circuit (S2). Then, the assist microprocessor circuit 200 samples the cuff pressure voltage in real-time (S4), and corrects the measured result, that is, calculates the real-time pressure value based on the linear property of the pressure sensor (S5), and decides if the corrected pressure value exceeds the minimum safe pressure value (15 mmHg for "Adult", 5 mmHg for "Infant") (S6). If yes, the assist microprocessor circuit 200 decides whether or not a duration exceeds 180 seconds for "Adult", or 90 seconds for "Infant" (S7). If overtime occurs, the assist microprocessor circuit 200 will open the fast deflation valve 530 (S11) until the pressure is lowered to below the safety pressure (15 mmHg for "Adult", 5 mmHg for "Infant"). In this way, situations of endless inflation that may be caused by reasons such as a fault in the inflating timer of the main microprocessor during measurement can be avoided. If overtime doesn't occur, the assist microprocessor circuit 200 decides whether the air pump is in normal state (S8). If yes, the assist microprocessor circuit 200 decides whether the main microprocessor circuit 100 has a feed dog signal (S9). If no, the assist microprocessor circuit 200 outputs RESET signal while outputting a signal for closing the fast deflation valve (only when the assist microprocessor circuit 200 outputs a signal for closing the fast deflation valve, the control right for the fast deflation valve can be transferred to the main microprocessor circuit 100), and forcibly resets the main microprocessor circuit 100 (S10). After being reset, the main microprocessor circuit 100 outputs a control signal to open the fast deflation valve 530 and close the air pump, waiting for the next measurement.

Similarly, the assist microprocessor circuit 200 can meet the safety requirements for the intervals of the deflating time and the measurement time specified under requirements (4) and (5) of the above standards.

For Requirement (4) of the Above Standards:

In LONG TERM AUTOMATIC MODE, the assist microprocessor circuit 200 monitors the cuff pressure in real-time, and the time during which the cuff pressure is higher than the specified value (15 mmHg for "Adult", 5 mmHg for "Infant") will be accumulated for each inflation or deflation process (S12). Then, the assist microprocessor circuit 200 decides whether the deflating time exceeds 30 s, or the cuff pressure is lowered to below the specified value (15 mmHg for "Adult", 5 mmHg for "Infant") (S13). The accumulated time will be cleared and the deflation valve will be closed (S14), if the cuff pressure is lower than the specified value (15 mmHg for "Adult", 5 mmHg for "Infant"). When the accumulated time reaches the time specified under requirement (3) of the standards, the assist microprocessor circuit 200 will forcibly close the fast deflation valve 530.

For Requirement (5) of the Above Standards:

In LONG TERM AUTOMATIC MODE, under any SINGLE FAULT CONDITION, when the overpressure protection is activated, the assist microprocessor circuit 200 will monitor the deflation time of the apparatus and the cuff pressure value, until the deflation time exceeds 30 seconds or the cuff pressure is lowered to below the specified value (15 mmHg for "Adult", 5 mmHg for "Infant").

Thus, the requirements for safety protection of the non-invasive blood pressure measurement under the above standards are completely satisfied by timing control in combination with pressure measurement.

Monitor of Power Supply Voltage:

The assist microprocessor circuit 200 of the invention also samples the voltage of power supply. Since the output value of the assist pressure sensor for overpressure protection has a linear relationship with the voltage of power supply, the impact arisen from the fluctuation of the voltage of power supply can be corrected by sampling the voltage of power supply and introducing it when calculating the cuff pressure value. Assuming that: at the time of calibration of the overpressure protection point, the measured value of the voltage of power supply is P0, the pressure of the overpressure protection point is A0, the value of the voltage of power supply measured at real-time by the assist microprocessor circuit 200 is P, and the pressure measured at real-time is A. Taking the fluctuation of power supply into account, the cuff pressure value A can be corrected to A':

$$A' = A \times (P0/P)$$

Watchdog Functions:

The assist microprocessor circuit 200 functions as a watchdog for the main microprocessor circuit 100. In case of the program of the main microprocessor running out of control, the assist microprocessor circuit 200 can forcibly reset the main microprocessor while outputting a signal for closing the fast deflation valve. After being reset, the main microprocessor circuit 100 opens the fast deflation valve 530, and turn off the air pump 310, waiting for the next measurement. Under other situations when the assist microprocessor circuit 200 cannot get response from the main microprocessor circuit 100, the assist microprocessor circuit 200 can forcibly reset the main microprocessor circuit 100 via a reset signal line. If the main microprocessor circuit 100 cannot be reset normally, the assist microprocessor circuit 200 keeps monitoring the cuff pressure for ensuring the cuff pressure in safe range, and can alarm in form of sound and/or light.

It should be understood that the embodiment disclosed hereinabove is by way of illustration and example only and is not to be taken by way of limitation, the spirit and scope of the present invention being limited only by the term of the appended claims, rather than the above description, and intended to encompass any modifications falling within the meaning and range equivalent to that of the claims.

We claim:

1. A non-invasive blood pressure measurement apparatus, comprising:
    a main measurement circuit; and
    a safety protection circuit comprising at least one overpressure protection value and at least one pressurization timing value;
    wherein the main measurement circuit comprises:
        a main microprocessor circuit for receiving a first cuff pressure signal of a cuff and calculating a pressure value of the cuff;
        an air pump control circuit for receiving a first control signal from the main microprocessor circuit for controlling operation of an air pump based on the first cuff pressure signal; and
        a deflation valve control circuit for receiving a second control signal from the main microprocessor circuit for controlling operation of a deflation valve based on the first cuff pressure signal; and
    wherein the safety protection circuit comprises an assist microprocessor circuit for collecting a second cuff pressure signal of the cuff in real-time and determining a pressurization time under various modes of operation, for outputting a third control signal to the deflation valve control circuit depending on the second cuff pressure signal received from the assist pressure measurement circuit and the determined pressurization time, and for controlling operation of the deflation valve via the deflation valve control circuit based on a combination of the second cuff pressure signal and the determined pressurization time for a selected mode of operation;
    wherein the assist microprocessor circuit comprises:
        a signal input connected to a watchdog signal output of the main microprocessor circuit; and
        a control signal output connected to a reset signal input of the main microprocessor circuit;
    wherein when a program of the main microprocessor is dead, is running out of control, or fails to respond, the assist microprocessor circuit forcibly resets the main microprocessor by outputting a reset signal via the control signal output, and after being reset, the main microprocessor circuit outputs the second control signal to open the deflation valve and the first control signal to turn off the air pump.

2. The non-invasive blood pressure measurement apparatus of claim 1, wherein the assist microprocessor circuit comprises an air pump state monitoring port connected to an air pump control signal input of the air pump control circuit.

3. The non-invasive blood pressure measurement apparatus of claim 1, wherein the assist microprocessor circuit comprises a voltage sample signal input connected to a power supply for monitoring a voltage of the power supply.

4. The non-invasive blood pressure measurement apparatus of claim 1, further comprising a key module connected to the main microprocessor circuit and the assist microprocessor circuit, respectively, for inputting commands to the main microprocessor circuit and the assist microprocessor circuit.

5. The non-invasive blood pressure measurement apparatus of claim 1, further comprising a display module connected to the main microprocessor circuit for displaying one or both of the pressure value of the cuff and alarm information.

6. The non-invasive blood pressure measurement apparatus of claim 1, further comprising a communication interface module connected to the main microprocessor circuit and the assist microprocessor circuit, respectively, for allowing the main microprocessor circuit and the assist microprocessor circuit to communicate with external devices.

7. A safety protection method implemented by a non-invasive blood pressure measurement apparatus, the method comprising:
    respectively receiving cuff pressure signals by a main microprocessor circuit and an assist microprocessor circuit;
    outputting a control signal according to the respectively received cuff pressure signals by the main microprocessor circuit or the assist microprocessor circuit;
    receiving the control signal output from the main microprocessor circuit or the assist microprocessor circuit by a deflation valve control circuit;
    controlling operation of a deflation valve using the deflation valve control circuit according to the control signal output from the main microprocessor circuit or the assist microprocessor circuit; and
    upon detecting a fault condition, using the assist microprocessor circuit to reset the main microprocessor circuit.

8. The safety protection method of claim 7, wherein outputting the control signal by the assist microprocessor circuit comprises:

comparing, using the assist microprocessor circuit, the cuff pressure signal received from the assist pressure measurement circuit with a specified overpressure protection value; and if the specified overpressure protection value is exceeded, using the assist microprocessor circuit to output a control signal to the deflation valve control circuit so as to open the deflation valve until the pressure falls below a safety pressure.

9. The safety protection method of claim 7, wherein outputting the control signal by the assist microprocessor circuit comprises:

deciding, using the assist microprocessor circuit, if the cuff pressure signal received from the assist pressure measurement circuit exceeds a minimum safe pressure value;

if the minimum safe pressure value is exceeded, using the assist microprocessor circuit to initiate timing and to compare a duration in which the minimum safe pressure value is exceeded with a specified time under various measurement modes.

10. The safety protection method of claim 7, wherein outputting the control signal by the assist microprocessor circuit comprises:

if the duration exceeds the specified time, using the assist microprocessor circuit to output the control signal to the deflation valve control circuit so as to open the deflation valve until the pressure falls below a safety pressure.

11. The safety protection method of claim 7, wherein resetting the main microprocessor circuit comprises:

receiving a watchdog signal from the main microprocessor circuit by the assist microprocessor circuit;

outputting a reset signal by the assist microprocessor circuit to forcibly reset the main microprocessor circuit when a program of the main microprocessor circuit is dead, is running out of control, or fails to respond; and outputting the control signal to the deflation valve control circuit by the main microprocessor circuit so as to open the deflation valve and turn off an air pump.

12. The safety protection method of claim 7, further comprising:

calculating a cuff pressure using at least one of the cuff pressure signals;

sampling a voltage of a power supply using the assist microprocessor circuit; and using the voltage of the power supply to correct the calculated cuff pressure.

13. The safety protection method of claim 7, further comprising:

outputting, before the step of respectively collecting the cuff pressure signals, the control signal to the deflation valve control circuit from the from the assist microprocessor circuit every time the non-invasive blood measurement apparatus is powered up so that the deflation valve is opened and the cuff is communicated with the atmosphere; and measuring the atmospheric pressure at that time for eliminating a null drift by the assist microprocessor circuit.

14. The safety protection method of claim 7, wherein outputting the control signal by the assist microprocessor circuit comprises:

monitoring a cuff pressure using the assist microprocessor in real-time;

for each inflation and deflation of the cuff, accumulating, using the assist microprocessor circuit, a time during which the cuff pressure is higher than a specified value;

when the cuff pressure is lower than the specified value, clearing the accumulated time; and when the accumulated time reaches a specified time, outputting the control signal from the assist microprocessor circuit to the deflation valve control circuit to forcibly close the deflation valve.

* * * * *